United States Patent
Nishikaze

(10) Patent No.: US 10,877,043 B2
(45) Date of Patent: Dec. 29, 2020

(54) METHOD OF PREPARING SAMPLE FOR ANALYSIS AND ANALYSIS METHOD

(71) Applicant: SHIMADZU CORPORATION, Kyoto (JP)

(72) Inventor: Takashi Nishikaze, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 15/846,458

(22) Filed: Dec. 19, 2017

(65) Prior Publication Data

US 2018/0180627 A1 Jun. 28, 2018

(30) Foreign Application Priority Data

Dec. 28, 2016 (JP) ................. 2016-256350

(51) Int. Cl.
*G01N 33/68* (2006.01)

(52) U.S. Cl.
CPC ....... *G01N 33/6848* (2013.01); *G01N 27/622* (2013.01); *G01N 2400/00* (2013.01); *G01N 2440/38* (2013.01); *G01N 2560/00* (2013.01)

(58) Field of Classification Search
CPC .................................................. G01N 27/622
See application file for complete search history.

(56) References Cited

U.S. PATENT DOCUMENTS

| | | | |
|---|---|---|---|
| 6,228,654 | B1 | 5/2001 | Chait et al. |
| 9,333,247 | B2 * | 5/2016 | Moe ............. A61K 39/095 |
| 2010/0167326 | A1 | 7/2010 | Miyazaki et al. |
| 2015/0233903 | A1 | 8/2015 | Zhang et al. |
| 2018/0059094 | A1 | 3/2018 | Nishikaze |

FOREIGN PATENT DOCUMENTS

| | | |
|---|---|---|
| JP | 201376629 A | 4/2013 |
| JP | 201534712 A | 2/2015 |
| JP | 2015-535304 A | 12/2015 |
| JP | 2016194500 A | 11/2016 |
| WO | 2005016248 A2 | 2/2005 |
| WO | 2007/091627 A1 | 8/2007 |
| WO | 2010141918 A1 | 12/2010 |
| WO | 2014040066 A1 | 3/2014 |
| WO | 2016159291 A1 | 10/2016 |
| WO | 2016168612 A1 | 10/2016 |

OTHER PUBLICATIONS

Alley et al., J of Proteome Res., 2010, 9:3062-3072.*
Yang et al., Anal Chem, 2015, 87(19):9671-9678 or pp. 1-17 as printed/attached.*
Shah et al., Anal. Chem., 2013, 85:3606-3613.*
Wheeler, S. et al. Derivatization of sialic acids for stabilization in matrix-assisted laser desorption/ionization mass spectrometry and concomitant differentiation of a(2-3)- and a(2-6)-isomersRapid Communication in. Mass Spectrometry., 2009; pp. 303-312; vol. 23; United Kingdom.
Reiding, K. et al.; High-Throughput Profiling of Protein N-Glycosylation by MALDITOF-MS Employing Linkage-Specific Sialic Acid Esterification; Analytical Chemistry; 2014; pp. 5784-5793; vol. 86; Netherlands.
Dehaan, N. et al ; Linkage-Specific Sialic Acid Derivatization for MALDITOF-MS Profiling of IgG Glycopeptides; Analytical Chemistry; 2015; pp. 8284-8291; 2015; vol. 87; Netherlands.
Deok-Song Kim, et al.; "Both α2,3- and α2,6-Linked Sialic Acids on O-Linked Glycoproteins Act as Functional Receptors for Porcine Sapovirus", PLOS Pathogens, Jun. 5, 2014, vol. 10, No. 6 (16 pages total).
Li et al.; "MALDI-MS analysis of sialylated N-glycan linkage isomers using solid-phase two step derivatization method"; Analytica Chimica Acta; vol. 924 (2016); pp. 77-85.
Notice of Reasons for Refusal dated Feb. 12, 2020 from the Japanese Patent Office in Application No. 2016-256350.

* cited by examiner

*Primary Examiner* — Bin Shen
(74) *Attorney, Agent, or Firm* — Sughrue Mion, PLLC

(57) ABSTRACT

Disclosed is a method of preparing a sample that is suitably used for analysis of a glycoprotein or glycopeptide. A first reaction is performed to modify or remove at least one primary amino group contained in a peptide moiety of a glycopeptide or glycoprotein. Thereafter, a second reaction is performed. The second reaction is a reaction capable of modifying a carboxy group of sialic acid of a sugar chain. After the second reaction, a derivative from α2,3-linked sialic acid a derivative from α2,6-linked sialic acid have different masses. Determination of the presence or absence of sialic acid in the sugar chain of a glycoprotein or glycopeptide and identification of the linkage type of sialic acid can be simply performed by mass spectrometry.

12 Claims, 6 Drawing Sheets

METHOD OF PREPARING SAMPLE FOR ANALYSIS AND ANALYSIS METHOD

TECHNICAL FIELD

The present invention relates to a method of preparing a sample for analysis of a glycoprotein or glycopeptide, and an analysis method using the obtained sample.

BACKGROUND ART

Glycosylation of peptide chains is one of the most important processes of post-translational modification. Glycoproteins containing sugar chains attached to peptide chains are involved in various life phenomena. It is believed that, in vivo, intercellular signal transduction, molecular recognition, etc. are controlled by precisely recognizing slight structural differences of sugar chains attached to a protein. Therefore, structural analysis of glycoproteins or glycopeptides is expected to make a major contribution to elucidation of life phenomena, drug discovery, biomarker development, etc.

A sugar chain attached to a protein often has sialic acid. Sialic acids of sugar chain are directly involved in molecular recognition, and therefore the analytical determination of the presence or absence of sialic acid (the number of sialic acid residues) and the linkage type of sialic acid is important in structural analysis of glycoproteins or glycopeptides.

As sialic acid in a sugar chain, there are $\alpha$2,3-linked sialic acid and $\alpha$2,6-linked sialic acid (linkage isomers) that are different in their reducing end-side linkage type to a sugar residue. It is known that in vivo, a difference in the linkage type of sialic acid is involved in various life phenomena. For example, it is known that the linkage type of sialic acid changes with canceration. Therefore, identifying a difference in the linkage type of sialic acid is attracting attention as a biomarker or in quality control of biopharmaceuticals, etc.

For identifying the linkage type of sialic acid in a sugar chain, a method has been proposed in which derivatization is performed to form a derivative of sialic acid that is different in mass depending on the linkage type of sialic acid. For example, Toyoda (JP-A-2013-76629) proposes a method in which methylesterification of sialic acid is performed using 1-methyl-3-p-tolyltriazene (MTT), and then an acidic condition is created. According to this method, derivatives having different masses from $\alpha$2,3-linked sialic acid and $\alpha$2,6-linked sialic acid are obtained, because only $\alpha$2,3-linked sialic acid is selectively demethylated under an acidic condition. Wheeler et al (*Rapid Commun. Mass Spectrom.*, vol. 23, pp. 303-312 (2009)) and Reiding et al. (*Anal Chem.*, vol. 86, pp. 5784-5793 (2014)) disclose that by reacting a sugar chain in the presence of a dehydration-condensation agent and a nucleophile such as methanol or ethanol, the carboxy group of $\alpha$2,6-linked sialic acid is esterified by reaction with the nucleophile, and a lactone ring is formed from $\alpha$2,3-linked sialic acid by intramolecular dehydration. De Haan et al. (*Anal. Chem.*, vol. 87, pp. 8284-8291 (2015)) and Nishikaze (JP-A-2016-194500) disclose that by performing reaction in the presence of a dehydration-condensation agent and an amine as a nucleophile, the carboxy group of $\alpha$2,6-linked sialic acid is amidated by reaction with the nucleophile, and a lactone ring is formed from $\alpha$2,3-linked sialic acid by intramolecular dehydration.

The lactone formed by the intramolecular dehydration of an $\alpha$2,3-sialyl sugar chain is unstable, and therefore there is a case where when mixed with a matrix for MALDI-MS, the lactone is ring opened so that quantitativity of analysis is impaired. In the method proposed by Nishikaze, after the reaction in the presence of a dehydration-condensation agent (a carbodiimide such as N,N'-diisopropylcarbodiimide (DIC)) and isopropylamine, reaction is further performed in the presence of a phosphonium-based dehydration-condensation agent and methylamine to open the lactone ring to perform methylamidation. In this way, the quantitativity of analysis can be improved by forming a stabler derivative by ring opening of the lactone formed from an $\alpha$2,3-sialyl sugar chain.

Problems to be Solved by the Invention

Most of the reports that have heretofore been made about the identification of the linkage type of sialic acid by mass spectrometry relate to free sugar chains, and reports about examples of application to glycoproteins or glycopeptides are limited. In the presence of a dehydration-condensation agent and a nucleophile, there is a case where not only the carboxy group of sialic acid but also the C-terminal carboxy group of a peptide or the carboxy group of an acidic amino acid residue reacts with the dehydration-condensation agent. Further, there is a case where dehydration condensation occurs between the peptide N-terminal amino group or the amino group of a lysine residue and a carboxy group in the molecule.

These side reactions (dehydration and modification of a carboxy group) of a peptide moiety proceed in parallel with the modification reaction of the carboxy group of sialic acid of a sugar chain. The side reactions depend on the amino acid sequence, conformation, etc. of a peptide moiety. Therefore, it is not easy to predict what kind of side reaction occurs, and data analysis, such as assignment of peaks in a mass spectrum, becomes complicated. Further, when a side reaction proceeds halfway or two or more side reactions occur competitively, a very complicated mass spectrum is given due to a reduction in sensitivity caused by the splitting of the amount of ion for each product and the non-uniform structure of a sugar chain moiety. This may not only cause the loss of quantitativity but also make it impossible to even assign peaks.

As described above, Nishikaze discloses that in the presence of an amine and a dehydration-condensation agent, the carboxy group of a glycopeptide is less likely to be amidated, and the carboxy group of sialic acid is selectively modified (amidated or lactonized). However, in order to selectively modify the carboxy group of sialic acid without amidating the carboxy group of a glycopeptide, it is necessary to select reaction conditions such as the types and concentrations of dehydration-condensation agent and amine, the reaction temperature, the reaction time, etc. in detail depending on the structure of a sugar chain or the amino acid sequence of a peptide. When the reaction conditions are adjusted so that the rate of the linkage type-selective reaction of the carboxy group of sialic acid is increased, the carboxy group of a peptide moiety is likely to be amidated. Therefore, it is not easy to achieve both the identification of the linkage type of sialic acid and the inhibition of side reaction of a peptide moiety.

De Haan et al. disclose an example in which the linkage type of sialic acid in an IgG-derived glycopeptide was identified, and the reaction of carboxy groups present in a peptide has been clearly specified. Specifically, it is disclosed that the N-terminal glutamic acid of the peptide is intramolecularly dehydrated (pyroglutamylated), and the carboxy group of glutamic acid adjacent to the C-terminal side thereof and the C-terminal carboxy group of the peptide are dimethylamidated.

As will be described later in detail, the reaction of the carboxy group of a peptide moiety can be controlled only when the peptide moiety has a specific amino acid sequence like an IgG-derived peptide. As for the majority of amino acid sequences, it is not easy to predict the reaction of the carboxy group or amino group of a peptide moiety in the presence of a dehydration-condensation agent, and it is difficult to control two or more side reactions that competitively occur. In other words, the reaction for obtaining derivatives having different masses from α2,3-linked sialic acid and α2,6-linked sialic acid in a sugar chain moiety is based on the control of competitive reaction, and the control of both the competitive reaction against the carboxy group of sialic acid and the competitive reaction against the carboxy group of a peptide moiety at the same time is not easy except for a case where the peptide moiety has a specific amino acid sequence like an IgG-derived peptide.

In view of the above circumstances, an object of the present invention is to provide a universal analysis method capable of determining the presence or absence of sialic acid and identifying its linkage type in the sugar chain moiety of a glycoprotein or glycopeptide independently of the amino acid sequence of the peptide moiety.

SUMMARY OF THE INVENTION

The present invention relates to a method of preparing a sample for analysis of a glycoprotein or glycopeptide. In the present method, before a sialic acid linkage type-specific reaction is performed, a primary amino group contained in the peptide moiety of a glycopeptide or glycoprotein is modified or removed so as not to react with a carboxy group.

The present sample preparation method includes, in order: a first reaction for modifying or removing at least one primary amino group contained in a peptide moiety of a glycopeptide or glycoprotein; and a second reaction that is capable of modifying a carboxy group of sialic acid of a sugar chain.

The second reaction is a reaction in which α2,3-linked sialic acid and α2,6-linked sialic acid form derivatives having different masses. For example, the second reaction includes a reaction in which α2,3-linked sialic acid is selectively lactonized and a 2,6-linked sialic acid is selectively amidated or esterified. The second reaction may further include a reaction in which a lactone formed from α2,3-linked sialic acid is reacted with a nucleophile to form another derivative. In the reaction between a lactone and a nucleophile, the nucleophile is selected such that the resulting derivative has a different mass from the derivative formed by the reaction between α2,6-linked sialic acid and a nucleophile.

It is to be noted that the second reaction may be a reaction capable of modifying the carboxy group of sialic acid of a sugar chain. When the sugar chain of the glycopeptide as an analyte does not contain sialic acid, actual occurrence of modification of the carboxy group of sialic acid of the sugar chain is not required. In this case, by performing mass spectrometry, it can be determined that the sugar chain does not contain sialic acid. When the sugar chain contains only α2,3-linked sialic acid and does not contain α2,6-linked sialic acid, derivatization of α2,6-linked sialic acid does not occur in the second reaction. When the sugar chain contains only α2,6-linked sialic acid and does not contain α2,3-linked sialic acid, derivatization of α2,3-linked sialic acid does not occur in the second reaction.

Examples of the primary amino group contained in the peptide moiety include an ε-amino group of a lysine residue and a peptide N-terminal α-amino group. Hereinafter, unless otherwise specified, the primary amino group is simply referred to as "amino group".

The first reaction performed before the second reaction is a reaction for modifying or removing these amino groups, and is preferably a reaction for modifying an amino group. An example of the reaction for modifying an amino group includes a reaction in which at least one nitrogen-carbon bond is formed on a nitrogen atom of an amino group. Particularly, guanidinylation and/or dialkylation are/is preferred.

The first reaction is, for example, a reaction for modifying or removing an ε-amino group of a lysine residue contained in the peptide moiety. When the ε-amino group of a lysine residue is selectively modified, guanidinylation is preferred.

The first reaction is preferably a reaction for modifying all amino groups contained in the peptide moiety. Dialkylation of amino groups is preferred, and dimethylation is particularly preferred.

The first reaction may be performed in a state where the glycopeptide or glycoprotein is immobilized on a solid-phase carrier. The second reaction may be performed in a state where the glycopeptide or glycoprotein after subjected to the first reaction is immobilized on a solid-phase carrier.

Further, the present invention relates to analysis of a sample obtained by the above-described method. By subjecting a sample obtained by the above-described method to mass spectrometry, the sugar chain structure of a glycopeptide or glycoprotein can be analyzed.

By performing the second reaction after modifying or removing the primary amino group of the peptide by the first reaction, a side reaction between a carboxy group and the amine of the peptide in the second reaction can be inhibited. Therefore, peak splitting in a mass spectrum is reduced, and determination of the presence or absence of sialic acid in the sugar chain of a glycoprotein or glycopeptide and identification of the linkage type of sialic acid can be simply performed by mass spectrometry with a high degree of accuracy.

DETAILED DESCRIPTION OF EMBODIMENT

Figure 1A:
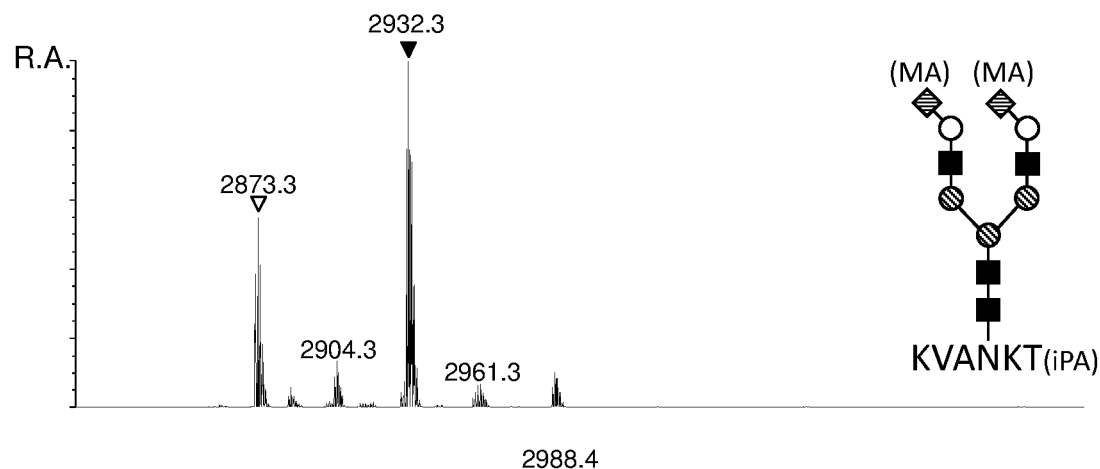
FIGS. 1A and 1B are mass spectra of reaction products of α2,3-SGP and α2,6-SGP in Example 1-1, respectively.

The present invention relates to a method of preparing a sample for analysis for analyzing the sugar chain structure of a glycopeptide or glycoprotein. A sample prepared by the present method is useful for analytically determining the presence or absence of sialic acid or the linkage type of sialic acid. The glycopeptide or glycoprotein is preferably one containing a sugar chain that may have sialic acid, such as an N-linked sugar chain or an O-linked sugar chain.

When the glycoprotein or glycopeptide has a large number of amino acid residues, the peptide chain is preferably cleaved into fragments having a length suitable for analysis by protease digestion or the like. For example, when a sample for mass spectrometry is prepared, the number of amino acid residues of the peptide chain is preferably 30 or less, more preferably 20 or less, even more preferably 15 or less. On the other hand, when it is required to clarify the origin of the peptide to which the sugar chain is bound, the number of amino acid residues of the peptide chain is preferably 2 or more, more preferably 3 or more.

Usually, a protease recognizes an amino acid sequence, and selectively proteolyzes a specific bond of a specific sequence. As such a protease, trypsin, lysyl endopeptidase (Lys-C), arginine endopeptidase, chymotrypsin, pepsin, or the like is used. It is to be noted that two or more proteases may be used in combination. Alternatively, a protease having low specificity such as thermolysin, proteinase K, or pronase E may be used. Conditions for the protease digestion are not particularly limited, and an appropriate protocol is used depending on the type of protease used. Prior to the protease digestion, denaturation treatment or alkylation treatment of a protein or a peptide in the sample may be performed. Conditions for the denaturation treatment or the alkylation treatment are not particularly limited, and known conditions are appropriately used. It is to be noted that the protease treatment may be performed after the first reaction and/or the second reaction is performed.

An amino group contained in the peptide moiety of the glycoprotein or glycopeptide as an analyte is modified or removed by a first reaction, and followed by a second reaction. For ease of comprehension, the second reaction will be described hereinbelow, and then the first reaction will be described.

[Second Reaction]

The second reaction in the present method is one capable of modifying the carboxy group of sialic acid of the sugar chain. The reaction (derivatization) that occurs at the carboxy group of α2,3-linked sialic acid and the reaction (derivatization) that occurs at the carboxy group of α2,6-linked sialic acid are different in the second reaction. As a result, a derivative formed from α2,3-linked sialic acid and a derivative formed from α2,6-linked sialic acid have different masses.

A specific example of the reaction in which α2,3-linked sialic acid and α2,6-linked sialic acid form derivatives having different masses include a nucleophilic reaction of the carbonyl of the carboxy group of sialic acid. The carboxy group of α2,3-linked sialic acid is present at a position where steric hindrance is larger as compared to the carboxy group of α2,6-linked sialic acid, and therefore a nucleophilic reaction of the carboxy group of α2,3-linked sialic acid with a nucleophile is less likely to occur. Therefore, in the reaction with a nucleophile such as an alcohol or an amine, α2,6-linked sialic acid is preferentially derivatized to form an ester or an amide. To be more specific, a derivative is formed from α2,6-linked sialic acid, while α2,3-linked sialic acid is not derivatized. By applying such a difference in reactivity, derivatives having different masses are produced.

In addition to the method in which only α2,6-linked sialic acid is selectively subjected to a nucleophilic reaction without subjecting α2,3-linked sialic acid to a nucleophilic reaction, there is a method in which a lactone is formed by intramolecular dehydration of α2,3-linked sialic acid using a dehydration-condensation agent. In the presence of a dehydration-condensation agent and a nucleophile, formation of a lactone ring by intramolecular dehydration and a reaction with the nucleophile competitively occur. In the vicinity of the carboxy group of α2,6-linked sialic acid, there is no hydroxyl group that can easily undergo intramolecular dehydration, and therefore in the presence of a nucleophile, a condensation reaction with the nucleophile preferentially occurs. On the other hand, in the case of α2,3-linked sialic acid, the access of a nucleophile to a carboxy group is inhibited by steric hindrance, and a hydroxyl group is present at a position where it can easily undergo intramolecular dehydration, and therefore a lactone is preferentially formed by intramolecular dehydration. Therefore, a lactone is preferentially formed from α2,3-linked sialic acid, and an amide or ester is preferentially formed from α2,6-linked sialic acid.

From the viewpoint of high selectivity for the linkage type of sialic acid, the second reaction is preferably a reaction in which in the presence of a dehydration-condensation agent and a nucleophile, α2,3-linked sialic acid is selectively lactonized, and α2,6-linked sialic acid is selectively amidated or esterified. A reaction in which an amine is used as a nucleophile to selectively amidate α2,6-linked sialic acid is particularly preferred.

A carbodiimide is preferable as the dehydration-condensation agent used in the reaction in which α2,3-linked sialic acid is selectively lactonized and α2,6-linked sialic acid is selectively amidated or esterified. Examples of the carbodiimide include N,N'-dicyclohexylcarbodiimide (DCC), N-(3-dimethylaminopropyl)-N'-ethylcarbodiimide (EDC), N,N'-diisopropylcarbodiimide (DIC), 1-tert-butyl-3-ethylcarbodiimide (BEC), N,N'-di-tert-butylcarbodiimide, 1,3-di-p-tolylcarbodiimide, bis(2,6-diisopropylphenyl)carbodiimide, bis(trimethylsilyl)carbodiimide, and 1,3-bis(2,2-dimethyl-1,3-dioxolan-4-ylmethyl)carbodiimide (BDDC), and salts thereof.

When an amidation reaction is performed using a carbodiimide as a dehydration-condensation agent and an amine as a nucleophile, α2,3-linked sialic acid is less likely to be amidated than when a phosphonium-based dehydration-condensation agent (so-called BOP reagent) or an uronium-based dehydration-condensation agent is used as a dehydration-condensation agent. Therefore, lactonization by intramolecular dehydration of α2,3-linked sialic acid preferentially occurs. On the other hand, amidation of the carboxy group of α2,6-linked sialic acid easily proceeds even when a carbodiimide is used as a dehydration-condensation agent.

In order to promote dehydration condensation, a highly nucleophilic additive is preferably used in addition to the carbodiimide. Preferred examples of the highly nucleophilic additive to be used include 1-hydroxybenzotriazole (HOBO, 1-hydroxy-7-aza-benzotriazole (HOAt), 4-(dimethylamino) pyridine (DMAP), ethyl 2-cyano-2-(hydroxyimino)acetate (CHA; trade name: OxymaPure), N-hydroxy-succinimide (HOSu), 6-chloro-1-hydroxy-benzotriazole (Cl-HoBt), and N-hydroxy-3,4-dihydro-4-oxo-1,2,3-benzotriazine (HOOBt).

Preferred examples of the amine include: ammonia; primary alkylamines such as methylamine, ethylamine, propylamine, isopropylamine, butylamine, sec-butylamine, and tert-butylamine; secondary alkylamines such as dimethylamine, ethylmethylamine, diethylamine, propylmethylamine, and isopropylmethylamine; and salts thereof.

From the viewpoint of high reactivity with the carboxy group of α2,6-linked sialic acid, the number of carbon atoms of the alkylamine (in the case of a secondary alkylamine, the total number of carbon atoms of two alkyl groups) is preferably 5 or less, more preferably 4 or less. On the other hand, in order to inhibit the amidation of the carboxy group of α2,3-linked sialic acid and increase the specificity for lactone formation, the number of carbon atoms of the alkylamine is preferably 2 or more.

Among the above-mentioned amines, when a primary amine is used, the reaction time can be shortened, and the specificity for lactone formation from α2,3-linked sialic acid tends to be high. Further, when an alkylamine having a branched alkyl group, especially isopropylamine is used, the specificity for lactone formation from α2,3-linked sialic acid tends to be high.

In the presence of a dehydration-condensation agent and an amine, sialic acid of the sugar chain is chemically modified so that a modified product is formed which is different depending on the linkage type of sialic acid. When performed in a liquid phase, the reaction in a non-aqueous solvent such as dimethylsulfoxide (DMSO) or dimethylformamide (DMF) is preferred. By performing the reaction in a non-aqueous solvent, a side reaction tends to be inhibited.

The concentration of each of the components in the liquid phase reaction is not particularly limited, and can be appropriately determined depending on the type of dehydration-condensation agent or amine used in the reaction. The concentration of the dehydration-condensation agent is, for example, preferably 1 mM to 5 M, more preferably 10 mM to 3 M. When a carbodiimide and a highly nucleophilic additive, such as HOAt or HOBt, are used in combination, their respective concentrations are preferably within the above range. The concentration of the amine is preferably 0.01 M to 20 M, more preferably 0.1 M to 10 M. The reaction temperature is preferably about −20° C. to 100° C., more preferably −10° C. to 50° C. Lowering the reaction temperature tends to enhance the specificity for lactone formation from α2,3-linked sialic acid. On the other hand, excessively lowering the reaction temperature reduces the reaction rate so that unreacted components tend to remain. Therefore, the reaction temperature or time is preferably adjusted depending on the type of amine used etc. so that the specificity for lactone formation is enhanced and the residual amounts of unreacted components are reduced. The reaction time may be determined depending on the concentrations of the sample and the reagents, As described above, the dehydration-condensation agent and the nucleophile used in the second reaction are preferably selected so that the carboxy group of sialic acid is subjected to reaction at a high rate. When a highly reactive dehydration-condensation agent and a highly-reactive nucleophile are used, not only the carboxy group of sialic acid but also the C-terminal carboxy group of the peptide or the carboxy group of an acidic amino acid residue (glutamic acid or aspartic acid) is modified.

In order to selectively derivatize the carboxy group of sialic acid while inhibiting the modification of the carboxy group of the peptide moiety, strict control of reaction conditions is required. When gentle reaction conditions are selected to strictly control the reaction, the reaction requires a long period of time. Further, it is not easy to completely inhibit the modification of a carboxy group contained in the peptide moiety such as the C-terminal carboxy group of the peptide or the carboxy group of an acidic amino acid residue while subjecting the carboxy group of sialic acid to reaction at a high rate. If some of carboxy groups contained in the peptide are not modified and remain unreacted, there is a case where data analysis is difficult due to peak splitting in a mass spectrum. Therefore, in the second reaction, a carboxy group contained in the peptide is also preferably modified in addition to the carboxy group of sialic acid. For example, the use of EDC as a dehydration-condensation agent makes it possible to selectively form a lactone derivative from α2,3-linked sialic acid, selectively amidate the carboxy group of α2,6-linked sialic acid and carboxy groups contained in the peptide, and reduce unreacted residual components.

The lactone formed from α2,3-linked sialic acid is easily hydrolyzed by an action of a dehydration-condensation agent. For example, when a liquid matrix is used for mass spectrometry, there is a case where some lactone rings open before measurement so that quantitativity is impaired. Therefore, a reaction for forming more stable derivative from the lactone formed from α2,3-linked sialic acid may be performed.

The derivative formed from the lactone is not particularly limited as long as it has a different mass from the derivative formed by the reaction between the carboxy group of α2,6-linked sialic acid and the nucleophile. From the viewpoint of high reactivity with the lactone, reaction with a nucleophile is preferred, and amidation using an amine is particularly preferred.

When the amine used for ring-opening amidation of the lactone has a different molecular weight from the amine used for the previous derivatization, the derivative formed by the reaction between α2,6-linked sialic acid and the amine and the derivative formed by ring-opening amidation of the lactone have different masses. An isotopically-labeled amine may be used to obtain amide derivatives having different masses.

From the viewpoint of facilitating reaction and enhancing quantitativity, an amine having high nucleophilic reactivity with the carbonyl of the lactone is preferably used for ring-opening amidation of the α2,3-linked sialic acid-derived lactone. Since the carbonyl of the α2,3-linked sialic acid-derived lactone is present in a site where steric hindrance is large, an amine having a small molecular volume is preferably used so that the nucleophilic reaction of the amine with the carbonyl is enhanced. Accordingly, ammonia, an alkylamine having 5 or less carbon atoms, or a salt thereof is preferably used for ring-opening amidation of the lactone. Further, the amine used for ring-opening amidation of the lactone is preferably one whose number of carbon atoms is smaller than that of the amine used for the previous reaction.

Preferred examples of the amine used in the ring-opening amidation of the lactone include: primary alkylamines such as ammonium salts, methylamine, ethylamine, propylamine, isopropylamine, butylamine, sec-butylamine, and tert-butylamine; secondary alkylamines such as dimethylamine, ethylmethylamine, diethylamine, propylmethylamine, and isopropylmethylamine; and salts thereof. The number of carbon atoms of the alkylamine is preferably 4 or less, more preferably 3 or less. Among the above-mentioned amines, primary alkylamines or salts thereof are preferred, linear primary alkylamines or salts thereof are more preferred, and methyl amine and ethyl amine or salts thereof are particularly preferred.

The amidation of the lactone is preferably performed in the presence of a dehydration-condensation agent. The dehydration-condensation agent is preferably one that highly efficiently reacts even with a carbonyl present in a site where steric hindrance is large. For example, the dehydration-condensation agent is preferably a phosphonium-based dehydration-condensation agent or an uronium-based dehydration-condensation agent.

Examples of the phosphonium-based dehydration-condensation agent include (benzotriazol-1-yloxy)tris(dimethylamino)phosphonium (BOP), benzotriazol-1-yl-oxy-tris(pyrrolidino)phosphonium hexafluorophosphate (PyBOP), bromo-tris(dimethylamino)phosphonium hexafluorophosphate (BroP), bromo-tris(pyrrolidino)phosphonium hexafluorophosphate (PyBroP), (7-azabenzotriazol-1-yloxy)tris(pyrrolidino)phosphonium hexafluorophosphate (PyAOP), and chloro-tris-pyrrolidinophosphonium hexafluorophosphate (PyCloP). They are collectively called "BOP reagents", and highly efficiently react even with a carboxy group present in a site where steric hindrance is large. Therefore, amidation can be performed with high reaction efficiency even on a site where steric hindrance is large, such as the carboxy group of α2,3-linked sialic acid or the carbonyl of the α2,3-linked sialic acid-derived lactone.

Examples of the uronium-based dehydration-condensation agent include (1-cyano-2-ethoxy-2-oxoethylideneaminooxy)dimethylamino-morpholino-carbenium hexafluorophosphate (COMU), 2-(1H-benzotriazole-1-yl)-1,1,3,3-hexafluorophosphate (HBTU), 2-(7-azabenzotriazol-1-yl)-1,1,3,3-hexafluorophosphate (HATU), 2-(1H-benzotriazole-1-yl)-1,1,3,3-tetramethyluronium tetrafluoroborate (TBTU), 2-(5-norbornene-2,3-dicarboximido)-1,1,3,3-tetramethyluronium tetrafluoroborate (TNTU), and O—(N-succinimidyl)-1,1,3,3-tetramethyluronium tetrafluoroborate (TSTU). Among these uronium salts, COMU is particularly preferred.

Among the above-mentioned dehydration-condensation agents, phosphonium-based dehydration-condensation agents are preferably used from the viewpoint of enhancing the amidation efficiency of the lactone. Further, in order to accelerate the reaction, a base such as N-methylmorpholine is preferably added so that its concentration is about 0.01 to 80% by weight of the total weight of a reaction system. By adding such a base to a reaction system at a concentration within the above range, reaction efficiency can be increased, and the occurrence of a side reaction, the precipitation of other reagents, etc. can be prevented. When N-methylmorpholine is contained as a base in a reaction system, its concentration is preferably 1 to 50% by weight, more preferably 10 to 40% by weight, even more preferably 15 to 30% by weight. Conditions for the amidation (reaction temperature, reaction time, etc.) are not particularly limited, and conventionally known conditions for amidation of sialic acid can be used without change.

After the ring-opening reaction of the α2,3-linked sialic acid-derived lactone is performed by hydrolysis, derivatization may be performed by reaction with a nucleophile. As described above, the lactone formed by the intramolecular dehydration of an α2,3-sialyl sugar chain can be hydrolyzed in water. In order to promote the ring opening of the lactone, an acid or a base is preferably used. Particularly, a base is preferably used because the lactone is easily hydrolyzed by a base. It is to be noted that when the amidation is performed after the ring opening of the lactone, it is preferred that the residual base does not inhibit the amidation or cause a side reaction. When the same amine as the amine used for the amidation after ring opening is used as the base, the above-described problem caused by the remaining base after the ring-opening reaction can be eliminated. It is to be noted that a hydrochloride is preferably used for the amidation, whereas an amine that is not in the form of a salt is preferably used as the base for promoting the ring opening of the lactone.

The ring opening of the lactone performed before the amidation by the second reaction reduces steric hindrance and facilitates the access of the amine to the carbonyl of sialic acid. Therefore, the ring opening performed before the amidation enhances the reaction efficiency of the amidation and reduces the amount of the residual lactone, which further enhances the accuracy of quantitative analysis.

As described above, the linkage type of sialic acid can be identified by forming derivatives having different masses from α2,3-linked sialic acid and α2,6-linked sialic acid and separating them from each other by mass spectrometry. Further, when the sugar chain does not have sialic acid, a derivative after the second reaction has a different mass from both the derivative formed from α2,3-linked sialic acid and the derivative formed from α2,6-linked sialic acid. Therefore, the presence or absence of sialic acid can also be determined.

However, when the second reaction is performed on the glycopeptide, in addition to the reaction of the carboxy group of sialic acid with a nucleophile and the formation of a lactone by intramolecular dehydration of sialic acid, the modification reaction of the amino group and carboxy group of the peptide may proceed. When such a side reaction proceeds halfway or two or more side reactions competitively occur, a reduction in sensitivity due to the splitting of the amount of ion for each product or a reduction in quantitativity occurs. Further, a mass spectrum becomes complicated due to peak splitting, which sometimes makes it difficult to perform analysis such as assignment of peaks.

As described above, peak splitting can be prevented by reacting the C-terminal carboxy group of the peptide or the carboxy group of an acidic amino acid residue with a nucleophile in the second reaction. On the other hand, the amino group of the peptide sometimes reacts with the carboxy group of sialic acid and the carboxy group of the peptide in the second reaction. The nucleophilic reaction of the amino group of the peptide with the carboxy group and the nucleophilic reaction of a nucleophile used in the second reaction with the carboxy group are competitive and cause peak splitting in a mass spectrum. For this reason, it is difficult to apply conventional methods for identifying the linkage type of sialic acid to glycoproteins or glycopeptides.

[First Reaction]

In the present method, prior to the second reaction, the first reaction is performed on the glycoprotein or glycopeptide to modify or remove at least one primary amino group contained in the peptide moiety. The modification or removal of an amino group contained in the peptide moiety prevents the occurrence of a side reaction, such as intramolecular dehydration between an amino group and a carboxy group, in the subsequent second reaction, Therefore, peak splitting is prevented and thus the accuracy of analysis by mass spectrometry is improved and data analysis is facilitated.

Examples of the removal of an amino group include treatment in which a C—N bond is cleaved such as Hoffman's elimination and treatment in which a lysine residue is removed from the peptide chain by cleaving the peptide in the vicinity of the C-terminus or N-terminus of the lysine residue by protease digestion using an endopeptidase such as lysyl endopeptidase or trypsin or an exopeptidase such as aminopeptidase or carboxypeptidase. Examples of the modification of an amino group include monoalkylation, dialkylation, amidation with an acetyl group, guanidinylation, nitrosation, diazotization, and cyanation.

The modification of an amino group may be performed by binding a tag or a linker to the N-terminal amino group of the peptide. An example of the linker includes a molecule that allows the N-terminal amino group of the peptide to selectively bind to the surface of a solid-phase carrier. An example of the tag includes a labeling reagent containing an N-hydroxysuccinimide (NHS) ester such as iTRAQ, iCAT, or TMT (Tandem Mass Tag).

From the viewpoint of ease and reliability of reaction, the first reaction is preferably a modification reaction of an amino group contained in the peptide. The amino group modification reaction is preferably a reaction that forms at least one nitrogen-carbon bond on the nitrogen atom of an amino group, such as monoalkylation, dialkylation, amidation, guanidinylation, or nitrosation, and is particularly preferably guanidinylation or dialkylation.

The guanidinylation of an amino group can be performed using a known guanidinylation reagent. Examples of the guanidinylation reagent include cyanamide, O-alkylisourea, S-alkylisothiourea, aminoiminomethanesulfonic acid, 1,3-bis(tert-butoxycarbonyl)-2-(trifluoromethylsulfonyOguanidine (Goodman's reagent), 1-amidinopyrazole hydrochloride, N,N'-bis(tert-butoxycarbonyl)-1H-pyrazole-1-carboxamidine, and N,N'-bis(carbobenzoxy)-1H-pyrazole-1-carboxamidine.

When S-alkylisothiourea, O-alkylisourea, or the like is used as a guanidinylation reagent, the reaction may be performed at about 0° C. to 90° C. in the presence of a base such as barium hydroxide, calcium hydroxide, magnesium hydroxide, sodium hydroxide, potassium hydroxide, lithium hydroxide, sodium hydrogen carbonate, sodium carbonate, or ammonia water; a tertiary amine such as triethylamine, N,N-dimethylaniline, N,N'-dimethylpiperazine, or N-methylpiperidine; or pyridine.

Examples of the dialkylation of an amino group include a reaction with an alkyl halide and a reaction using an aldehyde or a ketone (reductive amination). Among them, reductive amination is preferred because a side reaction is less likely to occur, and all the amino groups contained in the peptide can be dialkylated due to excellent reactivity.

Reductive amination is a reaction between an amine and an aldehyde or a ketone in the presence of a hydride reducing agent. When formaldehyde is used, an amino group is dimethylated. Examples of the reducing agent include sodium cyanoborohydride, sodium triacetoxyborohydride, borane pyridine, and formic acid. Particularly, reductive amination (Borch method) using sodium cyanoborohydride as a reducing agent is preferred from the viewpoint of reaction efficiency and reliability.

The glycoprotein or glycopeptide has an amino group at its N-terminus. Therefore, in the presence of a dehydration-condensation agent, intramolecular cyclization of the peptide easily occurs by the nucleophilic reaction of the N-terminal amino group with a carbonyl. Further, when lysine is contained in the amino acid sequence, intramolecular cyclization occurs by the nucleophilic reaction of the ε-amino group of lysine with a carbonyl in addition to the nucleophilic reaction of the N-terminal amino group with a carbonyl. Particularly, since the ε-amino group of lysine is far from the α carbon and has a high degree of freedom, an intermolecular cyclization easily occurs due to its high accessibility to the carbonyl of the C-terminal carboxy group of the peptide, the carboxy group of an acidic amino acid residue, the carboxy group of sialic acid, or the like.

When peptide fragments are prepared by protease digestion, trypsin or Lys-C is often used due to its high ability to recognize an amino acid sequence (sequence specificity). Trypsin selectively cleaves the C-terminal peptide bonds of arginine and lysine, and Lys-C selectively cleaves the C-terminal peptide bond of lysine. Therefore, peptide fragments obtained by protease digestion often have lysine at their C-termini.

When the ε-amino group of a lysine residue is previously removed or modified, intramolecular dehydration resulting from the amino group of a lysine residue does not occur in the second reaction. Therefore, peak splitting resulting from a side reaction is less likely to occur, so that the accuracy of analysis by mass spectrometry can be improved and data analysis is facilitated.

For example, protease digestion using carboxyendopeptidase can remove a lysine residue from a peptide having lysine at its C-terminus. A combination of treatment using Lys-C or trypsin and treatment using carboxyendopeptidase can remove a peptide C-terminal lysine residue to obtain a peptide containing no lysine residue.

As a method for selectively modifying the ε-amino group of lysine residue of the peptide, the above-described guanidinylation is suitable. Guanidinylation using O-alkylisourea or the like can achieve a rate of reaction with the ε-amino group of a lysine residue of almost 100%, and a reaction with the N-terminal amino group of the peptide hardly occurs. Accordingly, peak splitting resulting from the first reaction can be prevented.

By guanidinylating the ε-amino group of a lysine residue, the peptide moiety is positively charged, and therefore ionization of the peptide moiety is promoted in mass spectrometry. Therefore, guanidinylation of the ε-amino group of a lysine residue is advantageous in improvement of detection sensitivity of mass spectrometry.

It is preferable that the N-terminal amino group of the peptide as well as the amino group of a lysine residue contained in the peptide moiety is modified or removed in the first reaction. In other words it is preferable that all the amino groups contained in the peptide moiety are preferably modified in the first reaction. As described above, a method for modifying all the amino groups contained in the peptide moiety is preferably dialkylation of amino groups by reductive amination, particularly preferably dimethylation. As described above, the N-terminal amino group of the peptide may be modified by binding a tag, NHS, or the like to the N-terminus of the peptide.

The amino group of a lysine residue may be guanidinylated, while the N-terminal amino group of the peptide may be modified by another method. For example, after the guanidinylation of the amino group of a lysine residue, the N-terminal amino group of the peptide may be modified by reductive amination or the like. Alternatively, all the amino groups contained in the peptide may be modified by guanidinylating the amino group of a lysine residue in a state where the N-terminal amino group of the peptide is bound to a tag, a linker, or the like. As described above, the guanidinylation of the amino group of a lysine residue increases ionization efficiency in mass spectrometry, which tends to improve detection sensitivity.

As described above, by performing the first reaction before the second reaction, the occurrence of a side reaction or a competitive reaction in the second reaction can be inhibited, and thereby reducing peak splitting in a mass spectrum. Therefore, the sugar chain structure of the glycopeptide or glycoprotein can be analyzed with high accuracy. More specifically, the presence or absence of sialic acid in the sugar chain or the linkage type of sialic acid can be analytically determined with high accuracy.

According to the report by de Haan et al., in spite of the fact that a reaction corresponding to the first reaction in the present method is not performed, a derivative capable of identifying the linkage type of sialic acid is formed by the reaction of an IgG-derived peptide in the presence of ECD, HOBt, and dimethylamine (corresponding to the second reaction) with little side reaction. This is considered to be due to the fact that the glycopeptide as an analyte has a specific amino acid sequence that satisfies both: (1) there is no lysine residue; and (2) the C-terminal amino acid is glutamic acid.

In the amino acid sequence satisfying both (1) and (2), the only primary amino group contained in the peptide is the α-amino group of N-terminal glutamic acid. The α-amino group of N-terminal glutamic acid of the peptide reacts with the carboxy group of glutamic acid to give pyroglutamic acid (pyroglutamylation). Therefore, the nucleophilic reaction of the amino group of N-terminal glutamic acid with another carboxy group hardly occurs. Particularly, N-terminal glutamic acid is almost 100% pyroglutamylated in the presence of a dehydration-condensation agent, and therefore peak splitting resulting from its N-terminal α-amino group does not occur.

When the glycoprotein or glycopeptide does not have such a specific amino acid sequence as described above, i.e., when the glycoprotein or glycopeptide is a common one, the N-terminal amino group of the peptide mostly reacts with a carboxy group in the presence of a dehydration-condensation agent so that intramolecular cyclization occurs. Intramolecular cyclization by the reaction of the N-terminal amino group of the peptide is less likely to occur than intramolecular cyclization by the reaction of the amino group of a lysine residue. However, it is difficult to control or inhibit intramolecular cyclization except when the N-terminus of the peptide is glutamic acid (when pyroglutamylation occurs). Therefore, as described above, it is preferable that all the primary amino groups contained in the peptide moiety are modified or removed by the first reaction.

Other Reaction Embodiments

If necessary, the sample after the first reaction and the second reaction may be subjected to treatment such as purification, desalting, solubilization, concentration, or drying. These treatments can be performed using known methods.

The above-described first reaction and/or second reaction may be performed in a solid phase. When the first reaction is performed in a state where an glycopeptide or an glycoprotein is immobilized on a solid phase, the second reaction may be performed in a state where the glycopeptide or the glycoprotein after the first reaction remains immobilized on the solid phase. Alternatively, the glycopeptide or the glycoprotein after the first reaction may be immobilized on a solid phase, followed by the second reaction in the solid phase.

Any solid-phase carrier can be used without particular limitation as long as a glycopeptide or a glycoprotein can be immobilized. For example, in order to immobilize a glycopeptide or a glycoprotein, a solid-phase carrier having, as a ligand, an epoxy group, a tosyl group, a carboxy group, an amino group, or the like can be used. The glycopeptide or glycoprotein can be immobilized on a solid-phase carrier via, for example, its N-terminus, C-terminus, or SH group. As described above, the N-terminal amino group of the glycopeptide or glycoprotein may be immobilized on a solid-phase carrier via a linker having NHS. A solid-phase carrier having phenylboronic acid or the like as a ligand can be used to immobilize the sugar chain of the glycopeptide. Alternatively, the glycopeptide can be immobilized on a solid-phase carrier having a hydrazide group, an aminooxy group or the like as a ligand by oxidizing the sugar chain moiety.

After the first reaction and/or the second reaction are/is performed, the glycoprotein or glycopeptide immobilized on a solid-phase carrier may be collected by liberating the sample from the carrier by a chemical method, an enzymatic reaction, or the like. For example, the glycoprotein or glycopeptide immobilized on the carrier may be collected by enzymatically cleaving it by a protease or the like, or may be collected by liberating it by weakening its binding with a ligand with the use of an acid or a base. By performing the reaction in a state where the glycoprotein or glycopeptide is immobilized on a solid-phase carrier, removal of the reaction reagents or desalting purification is easier, and therefore sample preparation can be simplified.

[Analysis of Sample]

By subjecting the sample for analysis prepared by the above-described method to mass spectrometry, the linkage type of sialic acid can be identified, or information about sugar chain structure such as the ratio between linkage types or the presence or absence of sialic acid can be obtained. Examples of an ionization method for mass spectrometry include matrix-assisted laser desorption ionization (MALDI), electrospray ionization (ESI), and nano-electrospray ionization (nano-ESI). Particularly, MALDI is suitable. The analytical sample obtained by the present method can identify the linkage type of sialic acid in either positive ion mode or negative ion mode.

A sample separated by LC and detected as a peak may be subjected to mass spectrometry. When sample separation is performed by LC, LC-MS equipped with LC as a preliminary stage of mass spectrometry may be used, in which case an eluate from LC may be directly ionized and subjected to analysis. Alternatively, the eluate from the LC may be fractionated once and then subjected to mass spectrometry. An LC column is not particularly limited, and may be appropriately selected from, for example, hydrophobic columns such as C30, C18, C8, and C4 generally used for peptide analysis and carriers for hydrophilic affinity chromatography.

Mass spectrometry may be performed in multiple stages of $MS^2$ or more. By performing multi-stage mass spectrometry such as $MS^2$ or more, the structure of a sugar chain or the structure of a peptide moiety to which a sugar chain is bound can also be analyzed in addition to the linkage type of sialic acid. The structural analysis may be performed by database search using spectral data.

EXAMPLES

Hereinafter, the present method will be specifically described with reference to examples, but the present invention is not limited to the following examples. In the following description, "%" represents % by weight unless otherwise specified.

Example 1: Derivatization of Sialyl Glycopeptide (SGP)

In Example 1, derivatization of α2,3-SGP and α2,6-SGP was performed to determine whether the linkage type of sialic acid could be identified by mass spectrometry. As α2,3-SGP and α2,6-SGP, glycopeptide reference standards (2865.8 Da) were used, both of which are available from FUSHIM1 Pharmaceutical Co., Ltd. The SGP dissolved in water was dispensed in aliquots of 1 nmol, and the solvent was removed by centrifugal concentration (SpeedVac) to dry the SGP. The SGP was subjected to derivatization.

Experimental Example 1-1: Derivatization of Sialic Acid without Modifying Amino Group

[Reaction with Isopropylamine in the Presence of Dehydration-Condensation Agent]
A DMSO solution of isopropylamine hydrochloride (iPA-HCl), 1-ethyl-3-(3-(dimethylamino)propyl)carbodiimide (EDC) hydrochloride, and 1-hydroxybenzotriazole (HOBt) was prepared so that their respective final concentrations were 2 M, 500 mM, and 500 mM, and was added to the dried SGP. The mixture was reacted with stirring at room temperature for 1 hour, and was then diluted by adding 130 μL of acetonitrile (ACN) and 30 μL of an 80% ACN, 0.4% trifluoroacetic acid (TFA).

[Purification of Sample]
As a carrier for purification, GL-Tip Amide (manufactured by GL Science Inc.) was used. GL-Tip Amide was attached to a centrifuge adapter, and 100 μL of a 90% ACN, 0.1% TFA was added and passed through by centrifugation. Then, 100 μL of water was added and passed through by centrifugation, which was repeated three times. Thereafter, 100 μL of a 90% ACN, 0.1% TFA was added and passed through by centrifugation to equilibrate the carrier. Then, 180 μL of the diluted reaction solution was added to adsorb the sample onto the carrier, followed by centrifugation. Then, 180 μL of a 90% ACN, 0.1% TFA was added and passed through by centrifugation, which was repeated three times to perform washing. Finally, 10 μL of water was added and passed through by centrifugation, which was repeated twice. Then, 10 μL of a 0.1% aqueous TFA solution was further added and passed through by centrifugation to elute the sample. An appropriate amount of a 40% aqueous methylamine solution was added to a mixture of the three eluates so that the concentration of methylamine was 1%, and the mixture was dried by SpeedVac.

[Reaction with Methylamine and Purification]
A DMSO solution of methylamine hydrochloride (MA-HCl), benzotriazol-1-yloxytris(pyrrolidino)phosphonium hexafluorophosphate (PyBOP), and N-methylmorpholine (NMM) was prepared so that their respective final concentrations were 1 M, 250 mM, and 15%, and was added to the dried sample. The mixture was reacted with stirring at room temperature for 1 hour, and was then diluted by adding 130 μL of ACN and 30 μL of an 80% ACN, 0.4% TFA. Then, using GL-Tip Amide, purification and elution were performed in the same manner as those performed after reaction with isopropylamine, and the eluate was dried by SpeedVac.

Figure 1B:
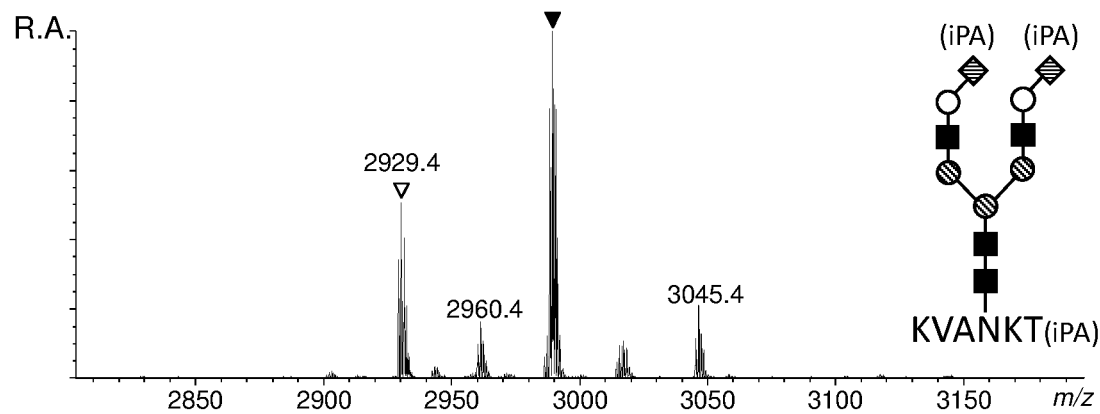

[Mass Spectrometry]
The dried sample was redissolved in 10 μL of water, 1 μL of the sample solution (100 pmol of the sample) was dropped onto a focus plate, and 0.5 μL of a solution obtained by dissolving 10 mg/mL 2,5-dihydroxybenzoic acid (DHBA), 0.1% methylenediphosphonic acid (MDPNA) in 50% ACN was added as a matrix. The solvent was removed by natural drying, and then mass spectrometry was performed in positive ion mode by MALDI-QIT-TOF-MS (AXIMA-Resonance, Shimadzu/Kratos). The mass spectrum of a reaction product of α2,3-SGP is shown in FIG. 1A, and the mass spectrum of a reaction product of α2,6-SGP is shown in FIG. 1B.

Experimental Example 1-2: Derivatization of Sialic Acid after Guanidinylation of Lysine Residue

[Guanidinylation of Lysine Residues of SGP]
First, 10.5 μL of 3.5 N ammonium hydroxide and 1.5 μL of a 50% aqueous O-methylisourea solution were added to the dried SGP, and the mixture was vortexed to dissolve the SGP. Then, the solution was heated on a heat block at 65° C. for 10 minutes to perform reaction.

[Purification]
The reaction solution was diluted to about 50 μL by adding 15 μL of a 10% aqueous TFA solution and water to perform desalting purification using a carbon column. As the carbon column, Stage Tip Carbon was used which was prepared by packing Empore disk carbon (manufactured by 3M) cut to have a diameter of about 1 mm in a 200-μL pipette tip. 100 μL of ACN was added to Stage Tip Carbon and then passed through by centrifugation. Thereafter, the same operation was repeated using 100 μL of 1 M NaOH, 100 μL of 1 M HCl, 100 μL of water, 100 μL of an 80% ACN, 0.1% TFA (twice), and 100 μL of water (twice) in this order to wash and equilibrate the column carrier. Then, the diluted reaction solution was added to the equilibrated column, and the solution was loaded by centrifugation. Thereafter, 150 μL of water was added and passed through by centrifugation, which was repeated three times to perform washing. Finally, 20 μL of an 80% ACN, 0.1% TFA solution was added and passed through by centrifugation, which was repeated twice to elute the sample. The thus obtained two eluates were mixed and dried to remove the solvent by SpeedVac.

Figure 2A:
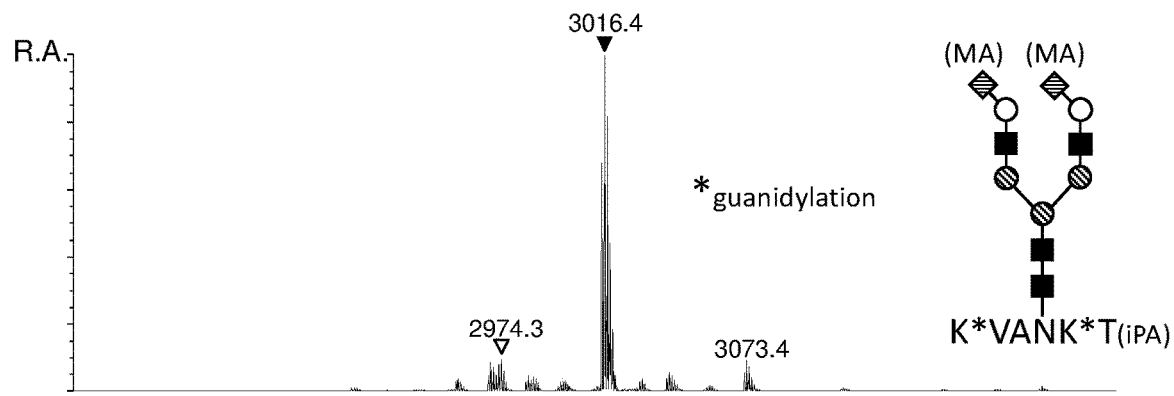
FIGS. 2A and 2B are mass spectra of reaction products of α2,3-SGP and α2,6-SGP in Example 1-2, respectively.
Figure 2B:
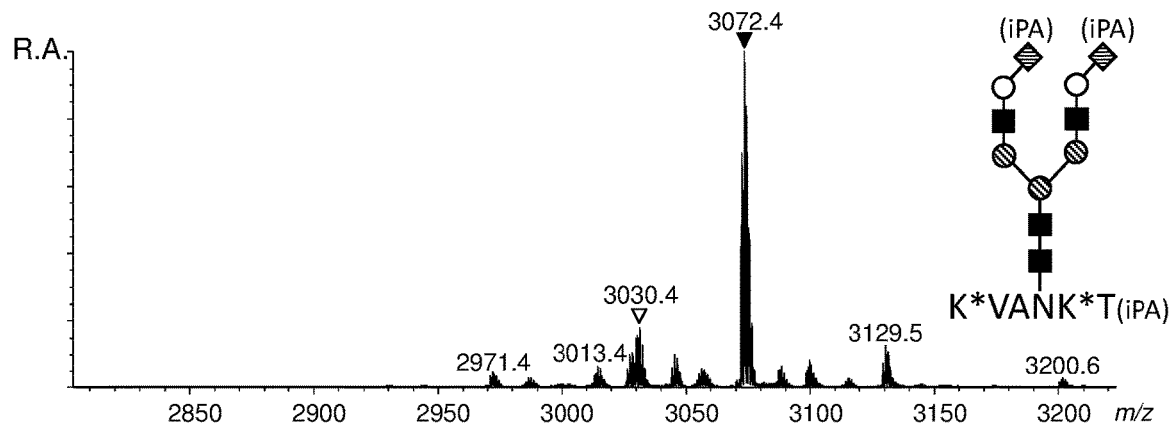

[Derivatization and Mass Spectrometry]
Using the sample after the reaction with O-methylisourea, derivatization was performed in the same manner as in Experimental Example 1-1 by the reaction with isopropylamine and the reaction with methylamine. Then, mass spectrometry was performed in positive ion mode. The mass spectrum of a reaction product of α2,3-SGP is shown in FIG. 2A, and the mass spectrum of a reaction product of α2,6-SGP is shown in FIG. 2B.

Experimental Example 1-3: Derivatization after Demethylation of all Amino Groups

[Dimethylation of Amino Groups]
First, 20 μL of a 100 mM triethylammonium bicarbonate (TEAB) buffer solution (pH 8.5) was added to the dried SGP. The mixture was vortexed to dissolve the SGP. Then, 1.6 μL of a 2% aqueous formaldehyde solution was added, and the mixture was gently vortexed and spun down. Then, 1.6 μL of a 300 mM aqueous sodium cyanoborohydride solution was added, and the mixture was reacted for 1 hour while gently vortexed at room temperature. Thereafter, 3.2 μL of 1% ammonia water was added for quenching, and the mixture was gently vortexed and spun down. Then, 1.6 μL of formic acid was added, and the mixture was gently vortexed and spun down. Finally, 72 μL of water was added, and desalting purification was performed using a carbon column in the same manner as in Experimental Example 1-2.

Figure 3A:
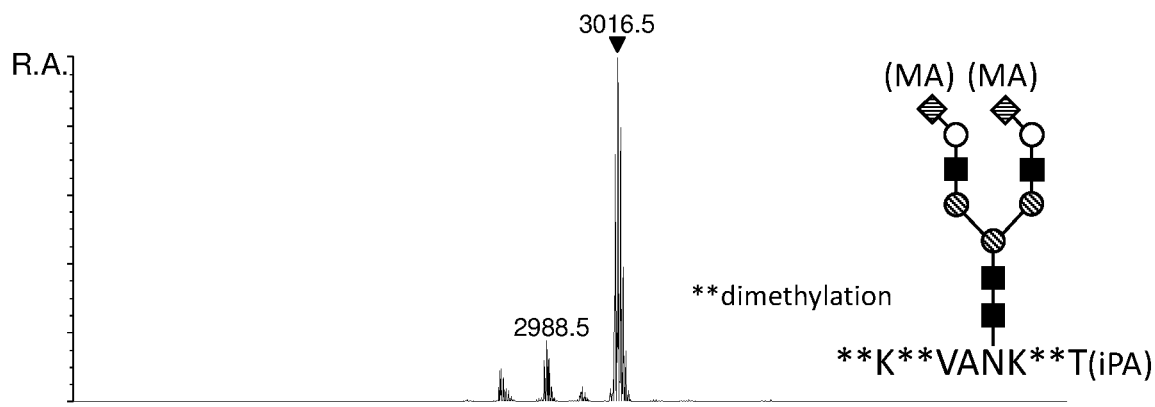
FIGS. 3A and 3B are mass spectra of reaction products of α2,3-SGP and α2,6-SGP in Example 1-3, respectively.
Figure 3B:
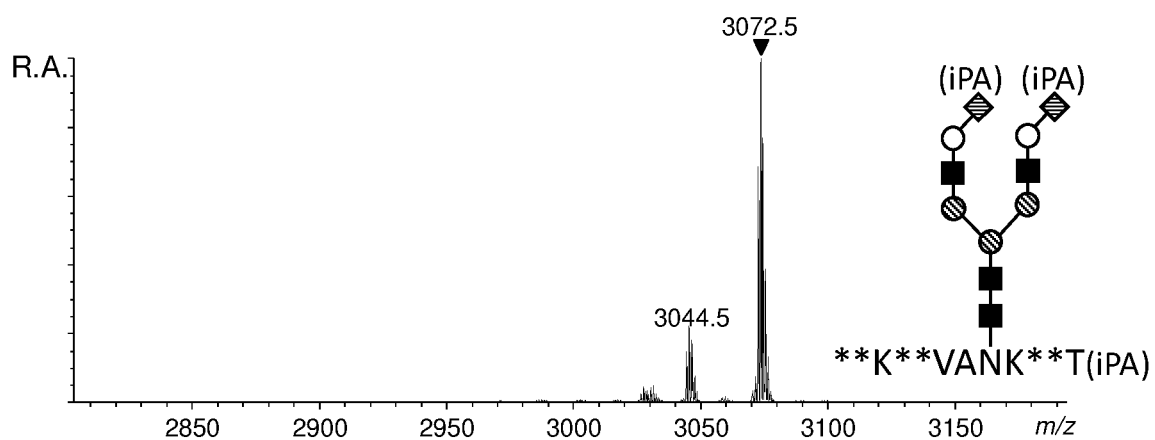

[Derivatization and Mass Spectrometry]
Using the sample after reductive amination reaction, derivatization was performed in the same manner as in Experimental Example 1-1 by the reaction with isopropylamine and the reaction with methylamine. Then, mass spectrometry was performed in positive ion mode. The mass spectrum of a reaction product of α2,3-SGP is shown in FIG. 3A, and the mass spectrum of a reaction product of α2,6-SGP is shown in FIG. 3B.

Experimental Example 1-4: Change in Time of Reaction with Isopropylamine

Figure 4A:
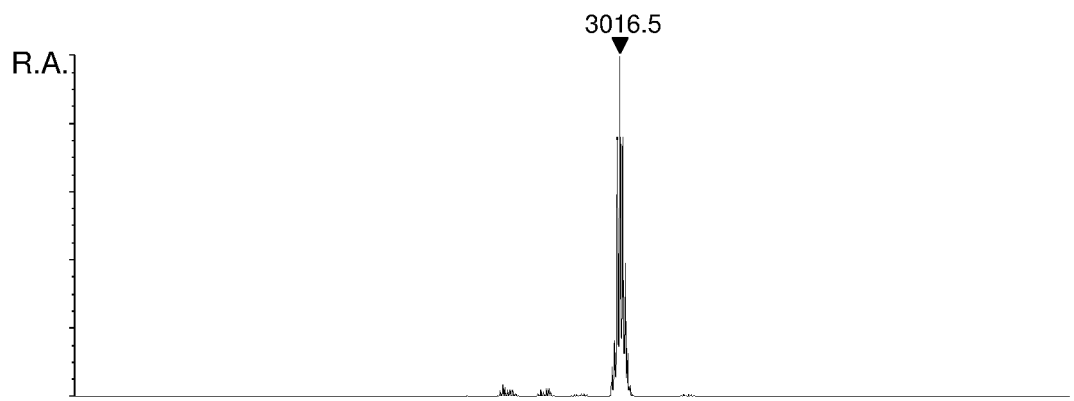
FIGS. 4A and 4B are mass spectra of reaction products of α2,3-SGP and α2,6-SGP in Example 1-4, respectively.
Figure 4B:
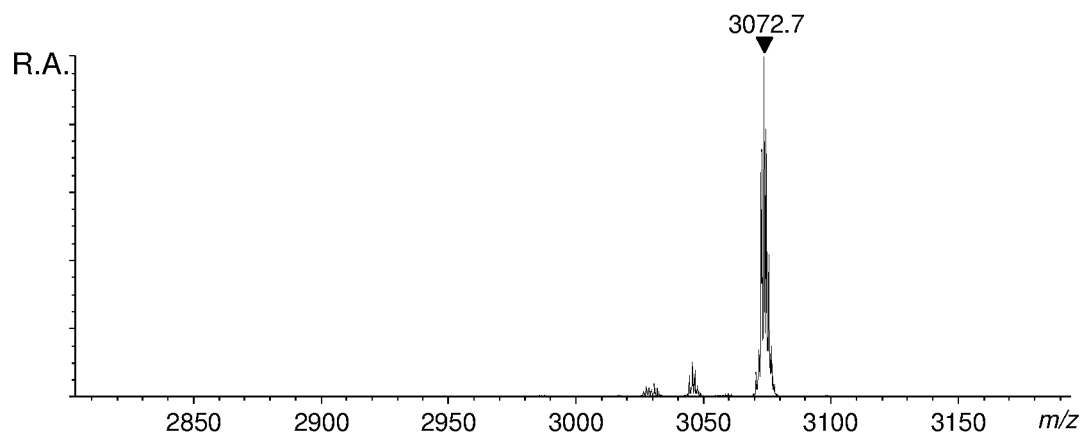

A sample was prepared in the same manner as in Experimental Example 1-3 except that the time of reaction of the sample after reductive amination reaction with isopropylamine was changed from 1 hour to 3 hours, and was then subjected to positive ion mode mass spectrometry. The mass spectrum of a reaction product of α2,3-SGP is shown in FIG. 4A, and the mass spectrum of a reaction product of α2,6-SGP is shown in FIG. 4B.

Evaluation of Mass Spectrum of Experimental Examples 1-1 to 1-4

In FIG. 1A, a peak was observed at m/z 2932 (denoted by ▼ in the mass spectrum) which was 67 Da larger than that of a peak derived from the SGP before derivatization. In FIG. 1B, a peak was observed at m/z 2988 (denoted by ▼ in the mass spectrum) which was 123 Da larger than that of a peak derived from the SGP before derivatization. The difference of 56 Da between these peaks is twice the difference between an isopropyl group and a methyl group. This reveals that the difference in m/z was caused by the fact that the carboxy groups of two α2,3-linked sialic acid residues of α2,3-SGP were methylamidated, whereas the carboxy groups of two α2,6-linked sialic acid residues of α2, 6-SGP were isopropylamidated.

Specifically, in the presence of EDC, HOBt, and iPA-HCl, the carboxy group of α2,6-linked sialic acid and the C-terminal carboxy group of the peptide are isopropylamidated, whereas α2,3-linked sialic acid is lactonized by intramolecular dehydration. The lactone formed from α2,3-linked sialic acid is ring opened and methylamidated by reaction with MA-HCl in the presence of PyBOP and NMM. The carboxy group of α2,6-linked sialic acid and the C-terminal carboxy group of the peptide do not react with methylamine after isopropylamidated. Therefore, a difference of 28 Da is caused per one sialic acid residue, which corresponds to the difference between an isopropyl group and a methyl group.

As described above, the linkage type of sialic acid can be identified by performing derivatization so that α2,3-linked sialic acid and α2,6-linked sialic acid form different derivatives. However, in FIGS. 1A and 1B, many contamination peaks were observed other than the peaks obtained by the above-described sialic acid linkage type-specific derivatization.

From MS/MS measurement (data not shown), it was confirmed that all these contamination peaks were derived from side reaction products of the peptide moiety. It was confirmed that the peak of m/z 2873 in FIG. 1A and the peak of m/z 2929 in FIG. 1B (denoted by ∇ in the mass spectra) were derived from a compound formed by intramolecular cyclization caused by dehydration condensation between the C-terminal carboxy group of the peptide and an amino group in the peptide without the occurrence of isopropylamidation of the C-terminal carboxy group of the peptide during the reaction with isopropylamine.

In FIG. 2A, a peak was observed at m/z 3016 (denoted by ▼ in the mass spectrum) which was 151 Da larger than that of a peak derived from the SGP before derivatization. In FIG. 2B, a peak was observed at m/z 3072 (denoted by ▼ in the mass spectrum) which was larger by 207 Da than that of a peak derived from the SGP before derivatization. The difference in m/z between them is 56 Da as in the case of Experimental Example 1-1. This reveals that a difference in molecular weight between the derivatives is caused by methylamidation of α2,3-linked sialic acid and isopropylamidation of α2,6-linked sialic acid.

In Experimental Example 1-2 (FIGS. 2A and 2B) in which the reaction with O-methylisourea was performed before the reaction with isopropylamine, the m/z of the main peaks derived from the derivatives were larger by 84 than those derived from the derivatives formed in Experimental Example 1-1 (FIGS. 1A and 1B). After the reaction with O-methylisourea, the SGP before the reaction with isopropylamine was subjected to mass spectrometry. As a result, it was found that the m/z of both peaks derived from α2,3-SGP and α2,6-SGP were increased by 84 than those derived from α2,3-SGP and α2,6-SGP before the reaction with O-methylisourea. It was confirmed that this difference of 84 Da was caused by the guanidinylation of amino groups of two lysine residues present in the peptide (increase by 42 Da per one amino group), and the N-terminal amino group of the peptide remained as an amino group without being derivatized.

In Experimental Example 1-2, peak splitting resulting from side reactions was inhibited as compared to that in Experimental Example 1-1, and peaks resulting from intramolecular cyclization between the C-terminal carboxy group of the peptide and the amino group of a lysine residue (denoted by ∇ in the mass spectra) were significantly reduced. These results reveal that when the amino group of a lysine residue in the peptide is guanidinylated before the derivatization of sialic acid, intramolecular cyclization caused by dehydration condensation between the C-terminal carboxy group of the peptide and the amino group of a lysine residue was inhibited. Since the intramolecular cyclization is inhibited, contamination peaks derived from the side reaction products of the peptide moiety are reduced so that the assignment of peaks can be facilitated leading to improvement of quantitativity of analysis.

In FIG. 3A, a peak was observed at m/z 3016 (denoted by ▼ in the mass spectrum) which was 151 Da larger than that of a peak derived from the SGP before derivatization. In FIG. 3B, a peak was observed at m/z 3072 (denoted by ▼ in the mass spectrum) which was 207 Da larger than that of a peak derived from the SGP before derivatization. The difference in m/z between them was 56 Da as in the case of Experimental Examples 1-1 and 1-2. This reveals that a difference in molecular weight between the derivatives is caused by methylamidation of α2,3-linked sialic acid and isopropylamidation of α2,6-linked sialic acid.

In Experimental Example 1-3 (FIGS. 3A and 3B) in which dimethylation of amino groups was performed by reductive amination (Borch reaction) using sodium cyanoborohydride before the reaction with isopropylamine, the m/z of the main peaks derived from the derivatives were larger by 84 than those derived from the derivatives formed in Experimental Example 1-1 (FIGS. 1A and 1B). After the reductive amination, the SGP before the reaction with isopropylamine was subjected to mass spectrometry. As a result, the m/z of both peaks derived from α2,3-SGP and α2,6-SGP were increased by 84 than those derived from α2,3-SGP and α2,6-SGP before the reaction, and peaks derived from side reaction products were not observed. The difference of 84 Da results from the fact that the amino groups of two lysine residues present in the peptide and the N-terminal amino group of the peptide (three amino groups in total) were all dimethylated (increased by 28 Da per one amino group).

In Experimental Example 1-3, the distribution of signals resulting from side reactions was significantly inhibited as compared to that in Experimental Example 1-1. A peak resulting from intramolecular cyclization between the C-terminal carboxy group of the peptide and the amino group of a lysine residue was not observed, which reveals that the distribution of signals was further inhibited as compared to that in Experimental Example 1-2.

In Experimental Example 1-4 in which the time of reaction with isopropylamine was increased, peak splitting was further inhibited as compared to that in Experimental Example 1-3. This is due to the fact that unreacted carboxy groups in the reaction with isopropylamine were reduced so that the formation of a derivative in which the C-terminal carboxy group of the peptide and the carboxy group of α2,6-linked sialic acid were methylamidated was inhibited.

The above results reveal that a main peak in a mass spectrum is concentrated at a target m/z and peak splitting is inhibited by modifying amino groups contained in the peptide by the first reaction before the second reaction is performed to form derivatives having different masses from α2,3-linked sialic acid and α2,6-linked sialic acid.

Example 2: Derivatization of Transferrin

In Example 2, derivatization of a glycopeptide derived from human transferrin, whose main component is an α2,6-sialyl sugar chain, was performed to determine whether the linkage type of sialic acid could be identified by mass spectrometry.

[Preparation of Transferrin-Derived Glycopeptide]

Figure 5A:
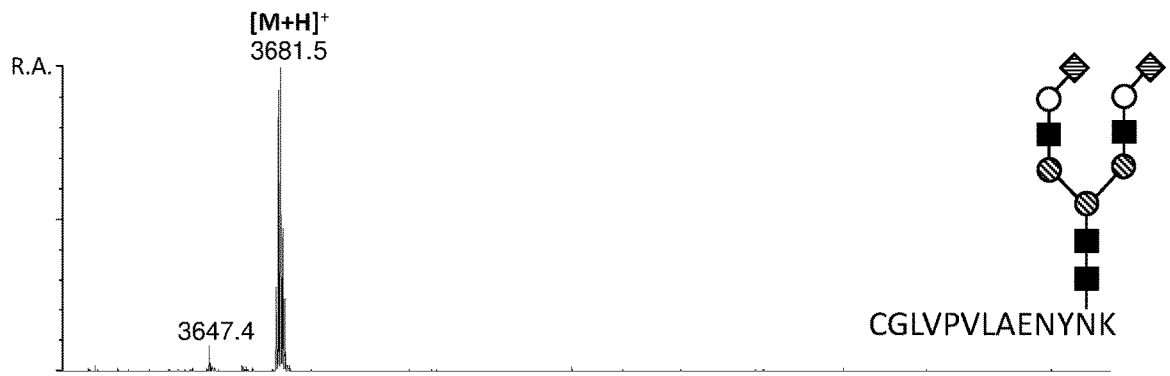
FIGS. 5A to 5C are mass spectra of a digest of transferrin and its derivatives obtained in Example 2.

Transferrin purchased from SIGMA was reacted in the presence of 6 M urea, 50 mM ammonium bicarbonate, and 5 mM tris(2-carboxyethyl)phosphine hydrochloride (TCEP) at room temperature for 45 minutes to perform denaturation and reduction. Then, reaction was performed in the presence of 10 mM iodoacetamide (IAA) at room temperature under light-tight conditions for 45 minutes to perform alkylation. Then, reaction was performed in the presence of 10 mM dithiothreitol (DTT) at room temperature under light-tight conditions for 45 minutes to deactivate excess IAA. Thereafter, trypsin was added, and reaction was performed at 37° C. overnight for protease digestion. After the protease digestion, peptides after digestion were separated by liquid chromatography to obtain a glycopeptide whose positive ion mass spectrum is shown in FIG. 5A.

Figure 5B:
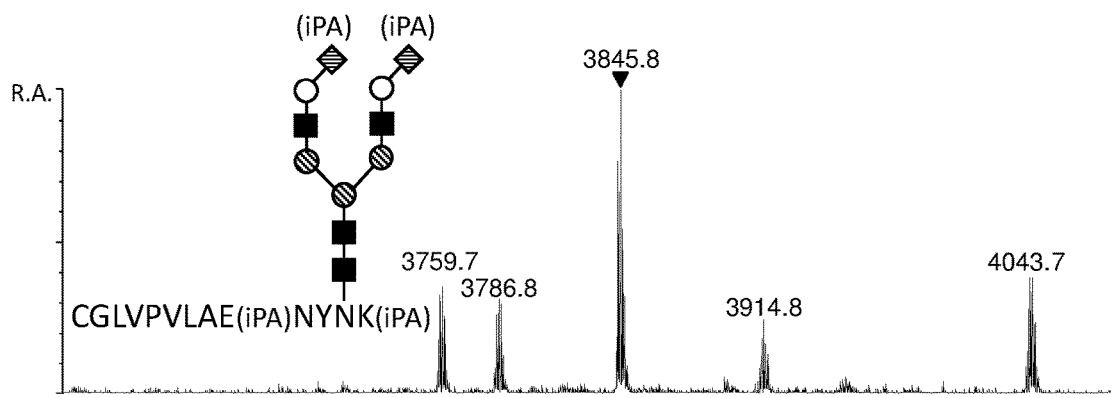

Experimental Example 2-1: Derivatization of Sialic Acid without Modification of Amino Group According to the same procedure as in Experimental Example 1-1 described above, the reaction in the presence of isopropylamine and the reaction in the presence of methylamine were performed in this order, and mass spectrometry was performed in positive ion mode. The thus obtained mass spectrum is shown in FIG. 5B.

Figure 5C:
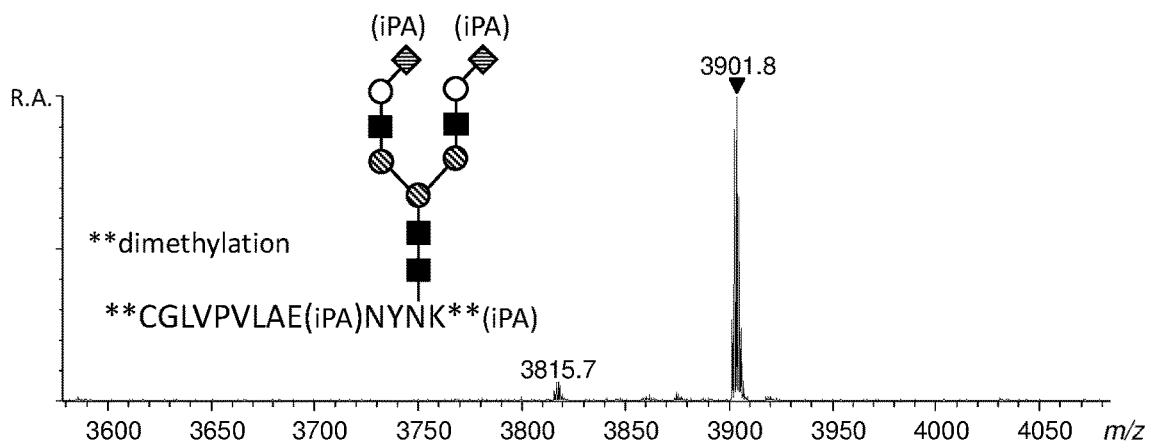

Experimental Example 2-2: Derivatization after Dimethylation of All Amino Groups According to the same procedure as in Experimental Example 1-3 described above, the reductive amination reaction was performed to dimethylate amino groups, and then the reaction in the presence of isopropylamine and the reaction in the presence of methylamine were performed in this order, and then mass spectrometry was performed in positive ion mode. The thus obtained mass spectrum is shown in FIG. 5C.

Evaluation of Mass Spectrum

In Experimental Example 2-1 (FIG. 5B), a peak was observed at m/z 3845 (164 Da larger than that of a peak derived from the glycopeptide before derivatization) which was derived from a derivative obtained by isopropylamidation of the carboxy groups of two α2,6-linked sialic acid residues, the carboxy group of a glutamic acid residue, and the C-terminal carboxy group of the peptide (four carboxy groups in total). However, many contamination peaks derived from side reaction products were also observed, and it was difficult to assign these contamination peaks.

On the other hand, in Experimental Example 2-2 (FIG. 5C) in which dimethylation of amino groups was performed, a strong peak was observed at m/z 3902 that was 220 Da larger than that of a peak derived from the glycopeptide before derivatization (FIG. 5A), and peak splitting resulting from side reaction products was hardly observed. The peak at m/z 3902 was assigned to a derivative obtained by isopropylamidation of the total of four carboxy groups in the glycopeptide and dimethylation of the amino group of a lysine residue and the N-terminal amino group of the peptide.

As in the case of Example 1, Example 2 reveals that a main peak in a mass spectrum is concentrated at a target m/z and peak splitting is inhibited by modifying amino groups contained in the peptide by the first reaction before the second reaction. The results of Example 1 and Example 2 reveal that the sample preparation by the present method is useful to identify the linkage type of sialic acid because even when the amino acid sequence of a peptide moiety is different, peak splitting can be inhibited.

Example 3: Derivatization of RNase B

In Example 3, derivatization of a glycopeptide derived from RNase B was performed to examine the effect of derivatization of a sialic acid-free glycopeptide.

[Preparation of Glycopeptide Derived from RNase B]

Figure 6A:
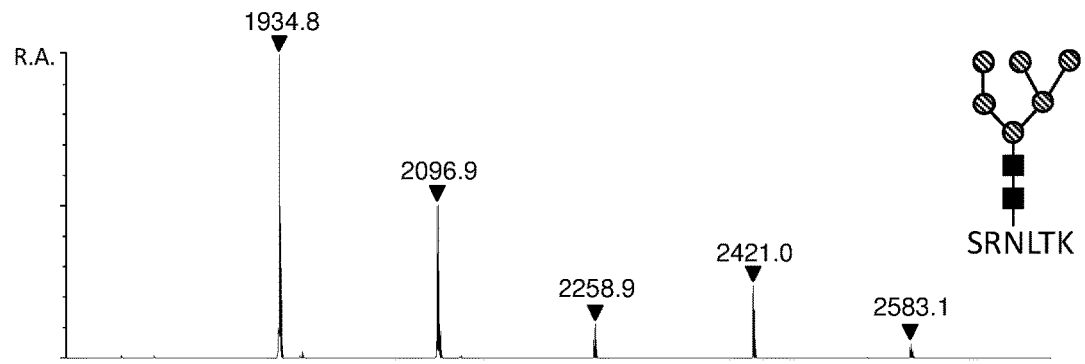
FIGS. 6A to 6C are mass spectra of a digest of RNase B and its derivatives obtained in Example 3.

RNase B purchased from SIGMA was used as a sample. The sample was subjected to reductive alkylation in the same manner as in Example 2, and then lysyl endopeptidase (Lys-C) was added to perform reaction at 37° C. overnight for protease digestion. After the protease digestion, desalting purification was performed using a carbon column. Then, purification and concentration were performed using GL-Tip Amide to obtain a glycopeptide having five high-mannose-type glycoforms (number of mannose residues: 5 to 9, 162 Da intervals). The positive ion mass spectrum of the glycopeptide is shown in FIG. 6A.

Figure 6B:
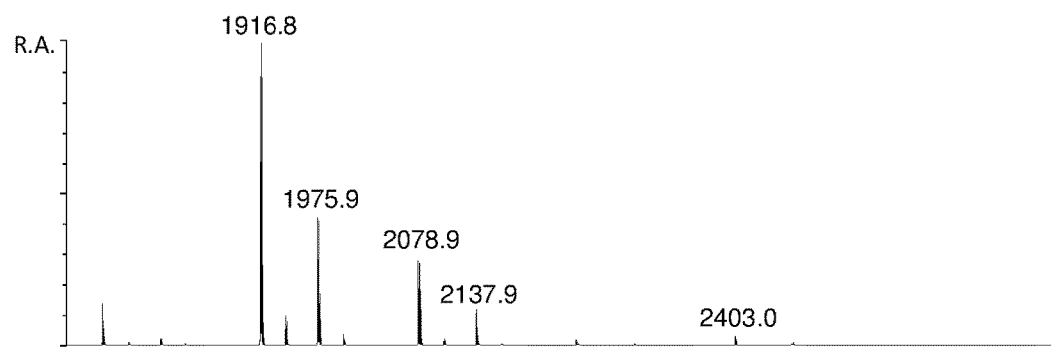

Experimental Example 3-1: Derivatization of Sialic Acid without Modification of Amino Group According to the same procedure as in Experimental Example 1-1 described above, the reaction in the presence of isopropylamine and the reaction in the presence of methylamine were performed in this order. Mass spectrometry was performed in positive ion mode. The thus obtained mass spectrum is shown in FIG. 6B.

Figure 6C:
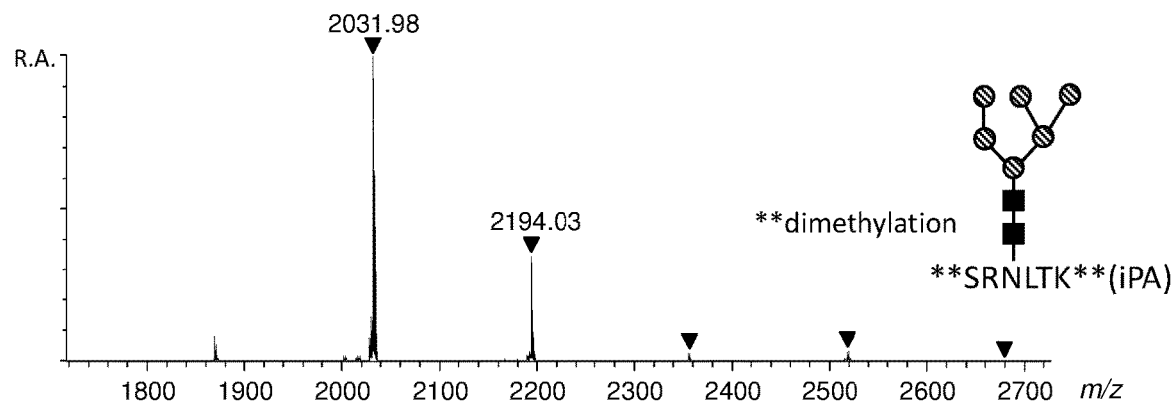

Experimental Example 3-2: Derivatization after Dimethylation of all Amino Groups According to the same procedure as in Experimental Example 1-3 described above, the reductive amination reaction was performed to dimethylate amino groups, and then the reaction in the presence of isopropylamine and the reaction in the presence of methylamine were performed in this order. Mass spectrometry was performed in positive ion mode. The thus obtained mass spectrum is shown in FIG. 6C.

Evaluation of Mass Spectrum

In Experimental Example 3-1 (FIG. 6B), the intensity of a peak at m/z 1935 was reduced as compared to that before the reaction (FIG. 6A), and a peak of m/z 1917 (−18) derived from a derivative formed by intramolecular cyclization, and a peak of m/z 1976 (+41) derived from a derivative formed by isopropylamidation were observed. The same applies to the other glycoforms, i.e., a peak derived from the unreacted glycopeptide, a peak derived from a derivative formed by intramolecular cyclization, and a peak derived from a derivative formed by isoproylamidation were mixed. As described above, when peak splitting resulting from a side reaction is caused by each of the glycoforms, a very complicated spectrum is obtained. In such a case, it is not easy to assign each of the peaks to any one of the glycoforms. Therefore, it is difficult to determine the presence or absence of sialic acid and to identify the linkage type of sialic acid.

In contrast, in Experimental Example 3-2 (FIG. 6C) in which dimethylation of amino groups was performed, peaks derived from five derivatives were observed whose m/z were 97 larger than those of peaks derived from the glycoforms before derivatization (FIG. 6A). These peaks were assigned to derivatives obtained by isopropylamidation of the C-terminal carboxy group of the peptide and dimethylation of the amino group of a lysine residue and the N-terminal amino group of the peptide. Peaks derived from side reaction products such as peaks derived from derivatives formed by intramolecular cyclization were hardly observed.

As shown in FIG. 6C, a difference in m/z between before and after derivatization of each of the five glycoforms is 97, and each of the peaks after derivatization is assigned to a derivative obtained by derivatization of the peptide moiety (dimethylation of two amino groups and iPA of one carboxy group). From this, it can be confirmed that the glycopeptide does not have sialic acid.

The glycopeptide used as an analyte in Example 3 has, in its peptide moiety, an arginine residue, which is a basic amino acid. In the first reaction, derivatization of the guanidyl group of arginine did not occur. Further, in the mass spectrum (FIG. 6C) after the second reaction, a peak derived from an intramolecular dehydration product between $NH_2$ of the guanidyl group of arginine and a carboxy group was not observed. This result confirmed that removal or derivatization of a guanidyl group, a secondary amino group, a tertiary amino group, and the like before the second reaction is not required, as long as a primary amino group contained in a peptide i.e., the ε-amino group of a lysine residue and the N-terminal α-amino group of a peptide are modified or removed by the first reaction.

The invention claimed is:

1. A method of preparing a sample for analysis of a glycoprotein or glycopeptide,
the method comprising, in order:
modifying or removing at least one primary amino group contained in a peptide moiety of a glycopeptide or glycoprotein; and
modifying a carboxy group of sialic acid of a sugar chain in the glycopeptide or glycoprotein, wherein α2,3-linked sialic acid is selectively lactonized and α2,6-linked sialic acid is selectively amidated so that the α2,3-linked sialic acid and the α2,6-linked sialic acid form derivatives having different masses
wherein the modification of the carboxy group of sialic acid occurs in the presence of a dehydration-condensation agent, an amine and an additive, the additive is selected from the group consisting of 1-hydroxybenzotriazole, 1-hydroxy-7-aza-benzotriazole, 4-(dimethylamino)pyridine, ethyl 2-cyano-2-(hydroxyimino)acetate, N-hydroxy-succinimide, 6-chloro-1-hydroxybenzotriazole, and N-hydroxy-3,4-dihydro-4-oxo-1,2,3-benzotriazine.

2. The method according to claim 1, wherein the first reaction includes formation of at least one nitrogen-carbon bond on a nitrogen atom of the primary amino group.

3. The method according to claim 1, wherein the first reaction includes at least one of guanidinylation and dialkylation of the primary amino group.

4. The method according to claim 1, wherein the first reaction includes modification or removal of a primary amino group of lysine residue contained in the peptide moiety.

5. The method according to claim 1, wherein the first reaction includes modification or removal of a peptide N-terminal primary amino group.

6. The method according to claim 1, wherein all primary amino groups contained in the peptide moiety are modified in the first reaction.

7. The method according to claim 6, wherein the primary amino groups are dialkylated in the first reaction.

8. The method according to claim 1, wherein the second reaction further includes a reaction in which a lactone formed from α2,3-linked sialic acid is reacted with the amine to form another derivative, and
the nucleophile in the second reaction is selected such that the derivative formed from the lactone and a derivative formed from the α2,6-linked sialic acid have different masses from each other.

9. The method according to claim 1, wherein the first reaction is performed in a state where the glycopeptide or glycoprotein is immobilized on a solid-phase carrier.

10. The method according to claim 1, wherein the second reaction is performed in a state where the glycopeptide or glycoprotein after subjected to the first reaction is immobilized on a solid-phase carrier.

11. A method of analyzing sugar chain structure of a glycopeptide or glycoprotein, comprising: preparation of a sample by the method according to claim 1; and analyzing the sample by a mass spectrometry.

12. The method according to claim 1, wherein the dehydration-condensation agent comprises a carbodiimide.

* * * * *